United States Patent [19]

Schwindeman

[11] Patent Number: 4,900,862

[45] Date of Patent: Feb. 13, 1990

[54] HERBICIDALLY ACTIVE SUBSTITUTED DIPHENYL ETHER OXIME DERIVATIVES

[75] Inventor: James A. Schwindeman, Canal Fulton, Ohio

[73] Assignee: American Cyanamid Company, Stamford, Conn.

[21] Appl. No.: 479,602

[22] Filed: Mar. 28, 1983

[51] Int. Cl.$^4$ .............................................. C07C 79/46
[52] U.S. Cl. ...................................... 560/21; 562/435; 71/111
[58] Field of Search .............................. 560/21; 71/111

[56] References Cited

U.S. PATENT DOCUMENTS 4,344,789  8/1982  Krass ..................................... 71/105

FOREIGN PATENT DOCUMENTS 2049695  12/1980  United Kingdom .................. 560/21

Primary Examiner—Paul J. Killos
Attorney, Agent, or Firm—Alice C. Brennan

[57] ABSTRACT

This invention relates to certain herbicidally active substituted diphenyl ether oxime derivatives, herbidical compositions of the same and the use thereof for pre-emergence and postermergence control of noxious plants, i.e., weeds.

4 Claims, No Drawings

HERBICIDALLY ACTIVE SUBSTITUTED DIPHENYL ETHER OXIME DERIVATIVES

FIELD OF THE INVENTION

This invention relates to certain substituted diphenyl ether oxime derivatives and to the use of same to control the growth of noxious plants, i.e., weeds.

DESCRIPTION OF THE INVENTION

This invention provides herbicidally active substituted diphenyl ether oxime compounds represented by the Formula I:

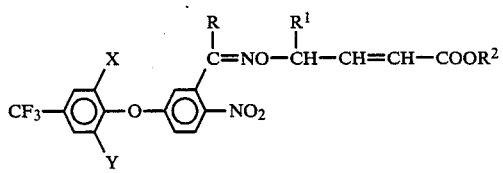

wherein:

X and Y are hydrogen or halogen provided that at least one of X or Y is halogen;

R is hydrogen or —$CH_2R^3$ wherein $R^3$ is hydrogen, halogen, $C_1$ to $C_3$ alkyl or haloalkyl, $C_1$ to $C_3$ alkoxy or alkylthio, mono or dialkylamino or cyano;

$R^1$ is hydrogen or $C_1$ to $C_3$ alkyl; and $R^2$ is hydrogen, alkali metal, $C_1$ to $C_4$ alkyl phenyl or up to $C_3$ alkenyl or alkynyL, ammonium or substituted ammonium.

Suitable alkyl radicals of which the various 'R' groups are representative include methyl, ethyl, n-propyl, iso-propyl, butyl, t-butyl or iso-butyl. Chloromethyl, chloroethyl, bromomethyl, bromoethyl, trifluoromethyl and the like are exemplary haloalkyls. As examples of alkoxy and alkylthio radicals there may be mentioned methoxy, ethoxy, propoxy, thiomethyl, thioethyl or the like. Mono or dialkyl amino groups include methylamino, diethylamino, methylethylamino, diethylamino or the like. Halogens represented by X, Y, Z and R include bromine, chlorine or fluorine, preferably bromine or chlorine. Sodium, potassium or lithium, preferably sodium or potassium, are exemplary of alkali metals represented by $R^2$. 2-propenyl and 2-propynyl are exemplary of preferred alkenyl and alkynyl radicals.

Prefered compounds of the Formula I are those wherein X is halogen, e.g., chlorine; Y is hydrogen; Z is nitro and $R^2$ is alkyl.

Compounds of the Formula I may be prepared using techniques known to and starting materials available to the art. For example, a Formula I compound may be prepared by reacting an appropriately substituted diphenyl ether oxime of the Formula II:

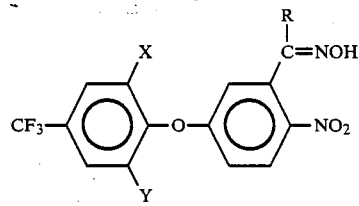

wherein X, Y and R are as previously defined, with an appropriately substituted halobutenoic acid or ester of the Formula III:

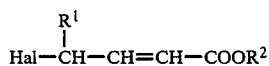

$R^1$ and $R^2$ are as previously defined and Hal is halogen, e.g., bromine or chlorine.

The following Example is illustrative of the preparation of a compound of this invention.

EXAMPLE

Preparation of 5-(2-chloro-4-trifluoromethylphenoxy)-2-nitroacetophenone oxime-O-[4-(2-butenoic acid, ethyl ester)].

A dry, 100 milliliter flask provided with a reflux condenser and a magnetic stirring bar was charged 4.20 grams (0.0112 mole) of 5-(2-chloro-4-trifluoromethylphenoxy)-2-nitroacetophenone oxime, 30 milliliters of dry acetonitrile, 5.16 grams (0.02 mole) of ethyl 4-bromocrotonate and 0.83 gram (0.005 mole) of anhydrous potassium iodide. The reaction mixture was stirred for 15 minutes and 2.07 grams (0.015 mole) of anhydrous potassium carbonate was added. After stirring at ambient temperature for about 18 hours, the reaction mixture was heated to reflux. After about 2 hours at reflux an additional 1.0 gram of ethyl 4-bromocrotonate and 0.5 gram of potassium carbonate were added and refluxing was continued. After cooling, the reaction mixture was transferred to a separatory funnel, diluted with 100 milliliters of pH 4 buffer solution and the pH of the mixture adjusted to about 3 with concentrated hydrochloric acid. The organic layer was drawn off and the aqueous layer was extracted with four 75 milliliter portions of ethyl acetate. The organic fractions were combined and dried over anhydrous magnesium sulfate. After solvent removal invacuo, the residue was purified by chromatography or silica gell using 9:1 V/$v$ hexane:ethyl acetate as the eluent affording 2.91 grams of a red oil identified by IR, NMR and MS analyses as 5-(2-chloro-4-trifluoromethylphenoxy)-2-nitroacetophenone oxime-O-[4-(2-butenoic acid, ethyl ester)].

Although the invention has been illustrated by the foregoing Example with regard to the preparation of a specific compound within the scope of Formula I, it is to be understood that other compounds within the scope of Formula I may readily be prepared by those skilled in the art simply by varying the choice of starting materials and using the same or similar techniques.

Weed control in accordance with this invention is effected by applying to the soil, before emergence of weeds therefrom or to the weed surface subsequent to emergence from the soil, a herbicidally effective amount of a compound of this invention. It is, of course, to be understood that the term "a compound of this invention" also includes mixtures of such compounds.

The term "herbicidally effective amount" is that amount of a compound of this invention required to so injure or damage weeds such that the weeds are incapable of recovering following application. The quantity of a compound of this invention applied in order to exhibit a satisfactory herbicidal effect may vary over a wide range and depends on a variety of factors, such as, for example, hardiness of a particular weed species, extent of weed infestation, climatic conditions, soil conditions, method of application, and the like. Typically, as little as one or less pound per acre of a compound of this invention would be expected to provide satisfactory weed control, although in some instances application rates in excess of one pound per acre; e.g., up to 5 or more pounds per acre might be required. Of course, the efficacy of a particular compound against a particular weed species may readily be determined by routine laboratory or field testing in a manner well known to the art. It is expected that satisfactory weed control can be had at a rate of application in the range of 1.0 to 1.0 pounds per acre.

Of course, a compound of this invention can be formulated according to routine methods with any of several known and commonly used herbicidal diluents, adjuvants and carriers. The formulations can contain liquid carriers and adjuvants such as organic solvents, as well as emulsifiers, stabilizers, dispersants, suspending agents, spreaders, penetrants, wetting agents and the like. Typical carriers utilized in dry formulations include clay, talc, diatomaceous earth, silica and the like. Preferred formulations are those in the form of wettable powders, flowables, dispersible granulates or aqueous emulsifiable concentrates which can be diluted with water at the site of application. Also, dry formulations such as granules, dusts, and the like, may be used.

When desired, a compound of this invention can be applied in combination with other herbicidal agents in an effort to achieve even broader vegetative control. Typical herbicides which can be conveniently combined with Formula I compound include atrazine, hexazione, metribuzin, ametryn, cyanazine, cyprazine, prometon, prometryn, propazine, simazine, terbutryn, propham, alachlor, acifluorfen, bentazon, metolachlor and N,N-dialkyl thiocarbamates such as EPTC, butylate or vernolate. These as well as other herbicides described, for example, in the *Herbicide Handbook of the Weed Society of America* may be used in combination with a compound or compounds of the invention. Typically such formulations will contain from about 5 to about 95 percent by weight of a compound of this invention.

The herbicidal formulations contemplated herein can be applied by any of several methods known to the art. Generally, the formulation will be surface applied as an aqueous spray. Such application can be carried out by conventional ground equipment, or if desired, the sprays can be aerially applied. Soil incorporation of such surface applied herbicides is accomplished by natural leaching, and is, of course, facilitated by natural rainfall and melting snow. If desired, however, the herbicides can be incorporated into the soil by conventional tillage means.

Compounds of this invention are believed effective for preemergence or postemergence control of a wide variety of broadleaf and grassy weeds. Typical of the various species of vegetative growth that may be controlled, combated, or eliminated are, for example, annuals such as pigweed, lambsquarters, foxtail, crabgrass, wild mustard, field pennycress, ryegrass, goose grass, chickweed, wild oats, velvetleaf, purslane, barnyardgrass, smartweed, knotweed, cocklebur, kochia, medic, ragweed, hemp nettle, spurrey, pondweed, carpetweed, morningglory, ducksalad, cheatgrass, fall panicum, jimsonweed, witchgrass, watergrass, wild turnip, and similar annual grasses and weeds. Biennials that may be controlled include wild barley, campion, burdock, bull thistle, roundleaved mallow, purple star thistle, and the like. Also controlled by the compounds of this invention are perennials such as quackgrass, Johnsongrass, Canada thistle, curly dock, field chickweed, dandelion, Russian knapweed aster, horetail ironweed, sesbania, cattail, wintercress, horsenettle, nutsedge, milkweed, sicklepod, and the like.

The compound prepared as described in the Example was tested for herbicidal efficacy, against a variety of broadleaf and grassy weed species, under controlled laboratory conditions of light, humidity and temperature. Solvent solutions of the compound were applied, both preemergence and postemergence to test flats containing the various weed species, and herbicidal efficacy was determined by visual inspection, periodically after application of the compounds. Herbicidal efficacy was determined on a scale of from 0 (no injury) to 10 (all plants dead). More particularly, the compound of the Example was found effective at a rate of application of 10 pounds per acre in preemergency control of teaweed, jimsonweed, wild mustard, coffeeweed, velvetleaf, tall morningglory, yellow foxtail, large crabgrass, Johnsongrass and wild oats, herbicidal injury ratings ranging from 7 to 10 having been observed up to 21 days subsequent to application.

At a postemergence rate of application of 10 pounds per acre, the compound of the Example was found effective against teaweed, jimsonweed, wild mustard, coffeeweed, velvetleaf and tall morningglory herbicidal injury ratings of from 8 to 10 having been observed up to 21 days subsequent to application.

Although the invention has been described in considerable detail by the foregoing, it is to be understood that many variations may be made therein by those skilled in the art without departing from the spirit and scope thereof as defined by the appended claims.

I claim:

1. A compound represented by the formula:

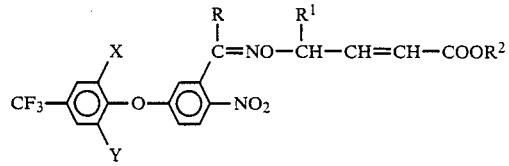

wherein:
X and Y are hydrogen or halogen provided that at least one of X or Y is halogen;
R is hydrogen or —$CH_2R^3$ wherein $R^3$ is hydrogen, halogen, $C_1$ to $C_3$ alkyl or haloalkyl, $C_1$ to $C_3$ alkoxy or alkylthio, mono or dialkylamino, or cyano;
$R^1$ is hydrogen or $C_1$ to $C_3$ alkyl; and
$R^2$ is hydrogen, alkali metal, $C_1$ to $C_3$ alkyl phenyl up to $C_3$ alkenyl or alkynyl, ammonium or substituted ammonium.

2. A compound of claim 1 that is 5-(2-chloro-4-trifluoromethylphenoxy)-2-nitroacetophenone oxime-O-[4-(2-butenoic acid, ethyl ester)].

3. A herbicidal composition containing abn inert carrier and a herbicidally effective amount of a compound or mixture of compounds defined in claim 1.

4. In a method of controlling weeds wherein a herbicidally effective amount of herbicide is applied to a growth medium prior to emergence of the weeds therefrom or the weeds subsequent to their emergence from the growth medium, wherein the improvement resides in using as the herbicide a compound or mixture of compounds defined by claim 1.

* * * * *